US008288114B2

(12) United States Patent
Honke et al.

(10) Patent No.: US 8,288,114 B2
(45) Date of Patent: Oct. 16, 2012

(54) METHOD FOR DETECTION OF COMPOUND INTERACTING WITH MOLECULE LOCATED ON CELL MEMBRANE

(75) Inventors: Koichi Honke, Nankoku (JP); Norihiro Kotani, Nankoku (JP); Naoyuki Taniguchi, Suita (JP)

(73) Assignees: Kochi University, Kochi (JP); Osaka University, Osaka (JP)

( * ) Notice: Subject to any disclaimer, the term of this patent is extended or adjusted under 35 U.S.C. 154(b) by 584 days.

(21) Appl. No.: 12/449,217

(22) PCT Filed: Jan. 24, 2008

(86) PCT No.: PCT/JP2008/051002
§ 371 (c)(1),
(2), (4) Date: Jul. 29, 2009

(87) PCT Pub. No.: WO2008/093595
PCT Pub. Date: Aug. 7, 2008

(65) Prior Publication Data
US 2010/0105568 A1    Apr. 29, 2010

(30) Foreign Application Priority Data
Jan. 29, 2007  (JP) ................................. 2007-017667

(51) Int. Cl.
*G01N 33/557*  (2006.01)
*G01N 33/536*  (2006.01)
(52) U.S. Cl. ......... 435/7.2; 435/7.5; 435/7.71; 436/517; 436/536; 436/56; 436/63; 436/173
(58) Field of Classification Search ................... 435/7.2, 435/7.5, 7.71, 7.9, 374; 436/517, 56, 63, 436/171, 172, 173, 536
See application file for complete search history.

(56) References Cited

U.S. PATENT DOCUMENTS
2005/0180945 A1    8/2005  Chaikof et al.
(Continued)

FOREIGN PATENT DOCUMENTS
JP    2005-24245    1/2005
(Continued)

OTHER PUBLICATIONS

Kotani et al. Biochemical Visualization of Cell Surface Molecular Clustering in Living Cells, PNAS 105 (21): 7405-7409 (May 27, 2008).*

(Continued)

*Primary Examiner* — Gail R Gabel
(74) *Attorney, Agent, or Firm* — Wenderoth, Lind & Ponack, L.L.P.

(57) ABSTRACT

The present invention aims to provide a convenient and low-cost method for detection of a wide variety of compounds interacting with a target molecule located on a cell membrane, using a living cell without need of separating the cell membrane or the like from the cell. The present invention also aims to provide a kit for carrying out the method of the present invention. The method for detection of the compound interacting with the molecule located on the cell membrane in the present invention comprises steps of, allowing a compound having a moiety capable of binding selectively to the molecule located on the cell membrane and a radicalization-promoting moiety, to act on the cell; further allowing a compound having a group capable of being radicalized by the radicalization-promoting moiety and a labeling group, to act on the cell; and identifying the interacting compound bound by the compound radicalized by the radicalization-promoting moiety.

6 Claims, 5 Drawing Sheets

(2)

U.S. PATENT DOCUMENTS

2006/0141496 A1     6/2006     Yabuuchi et al.

FOREIGN PATENT DOCUMENTS

| JP | 2005-522227 | 7/2005 |
|---|---|---|
| WO | 03/099835 | 12/2003 |

OTHER PUBLICATIONS

English translation of Chinese Office Action dated Oct. 19, 2011 issued in connection with the Chinese Application corresponding to the present U.S. Application.

Japanese Office Action entitled Notice of Reasons for Refusal (together with English translation) mailed Nov. 22, 2011 in corresponding Japanese Patent Application No. 2007-017667.

European Interview Summary prepared by the Examiner issued Mar. 3, 2011 in corresponding European Application No. 08 703 829.5.

Supplementary European Search Report issued Jun. 4, 2010 in European Application No. 08 70 3829 corresponding to the Present U.S. application.

Z.H. Zhong et al., "Insulin binding monitored by fluorescence correlation spectroscopy", Diabetologia, vol. 44, pp. 1184-1188, Sep. 1, 2001.

Amandio Vieira, "ELISA—Based Assay for Scatchard Analysis of Ligand-Receptor Interactions", Molecular Biotechnology, vol. 10, pp. 247-250, Dec. 1, 1998.

Norihiro Kotani et al., "Biochemical visualization of cell surface molecular clustering in living cells", Proceedings of the National Academy of Sciences USA (PNAS), vol. 105, No. 21, pp. 7405-7409, May 27, 2008.

European Official Communication issued Jun. 20, 2011 in corresponding European Patent Application No. 08703829.5.

International Search Report issued Mar. 4, 2008 in International (PCT) Application No. PCT/JP2008/051002.

Bower et al., "Cell Surface Antigens of Mycoplasma Species Bovine Group 7 Bind to and Activate Plasminogen", Infection and Immunity, Aug. 2003, vol. 71, No. 8, pp. 4823-4827.

Wijk et al., "Regulation of receptor protein-tyrosine phosphatase dimerization", Methods, 2005, vol. 35, pp. 73-79.

Liao et al., "Chromophore-assisted laser inactivation of proteins is mediated by the photogeneration of free radicals", Proc. Natl. Acad. Sci. USA, Mar. 1994, vol. 91, pp. 2659-2663.

Beck et al., "Fluorophore-assisted light inactivation: A high-throughput tool for direct target validation of proteins", Proteomics, 2002, vol. 2. pp. 247-255.

Kotani et al., "Biochemical Visualization of cis-Interactions between Cell Surface Molecules in Living Cells", Dai 27 Kai, The Japanese Society of Carboydrate Research Nenkai Yoshishu, Jul. 10, 2007, p. 164, P2-56.

Chinese Office Action issued Jul. 31, 2012 in corresponding Chinese Application No. 200880003314.X (with English translation).

\* cited by examiner

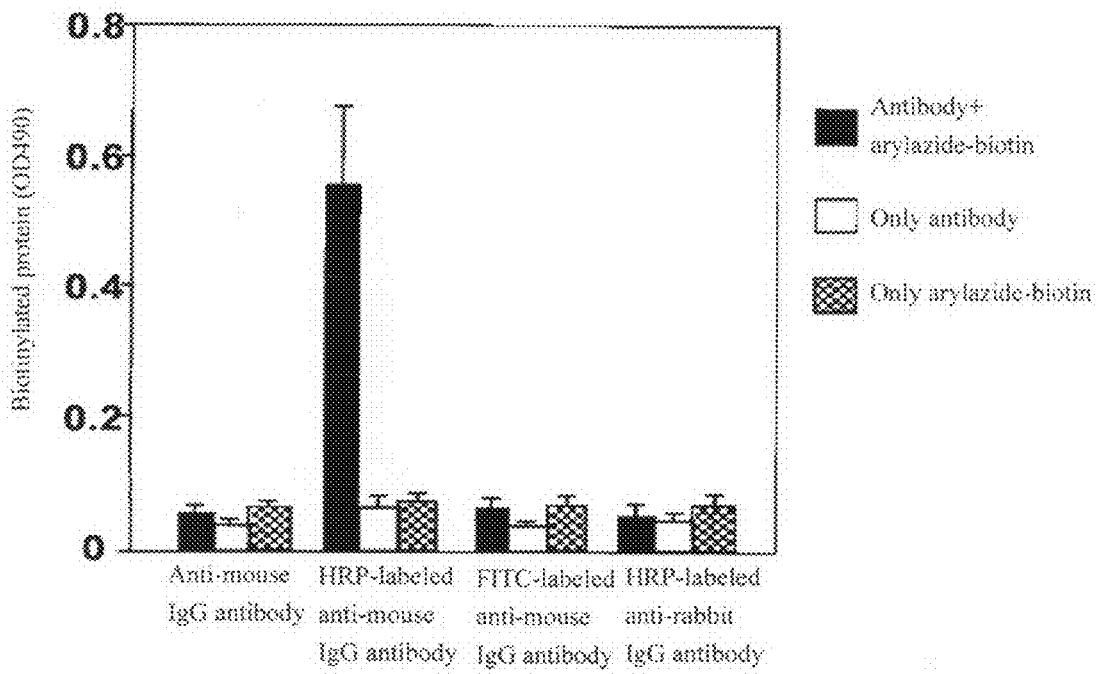
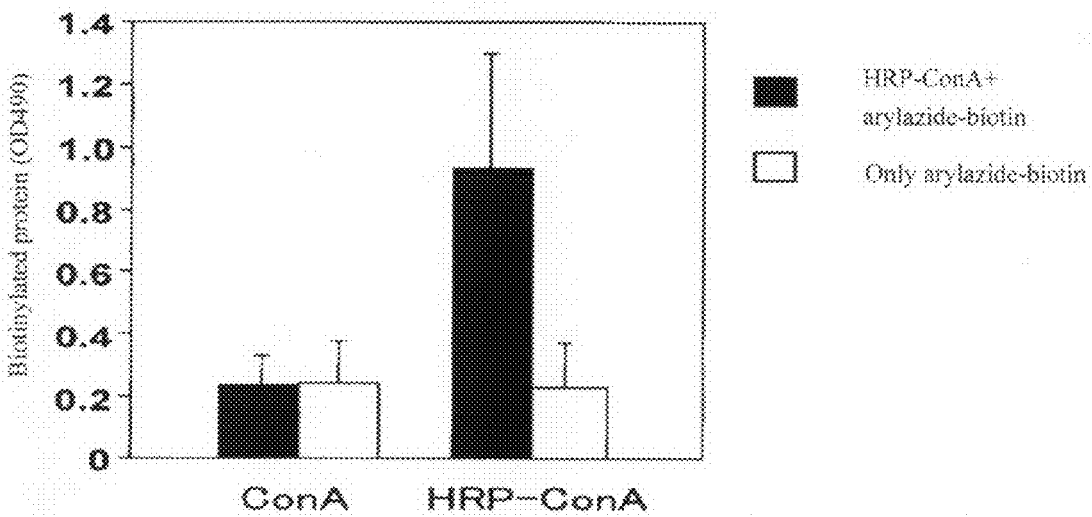

Fig.4
(1)
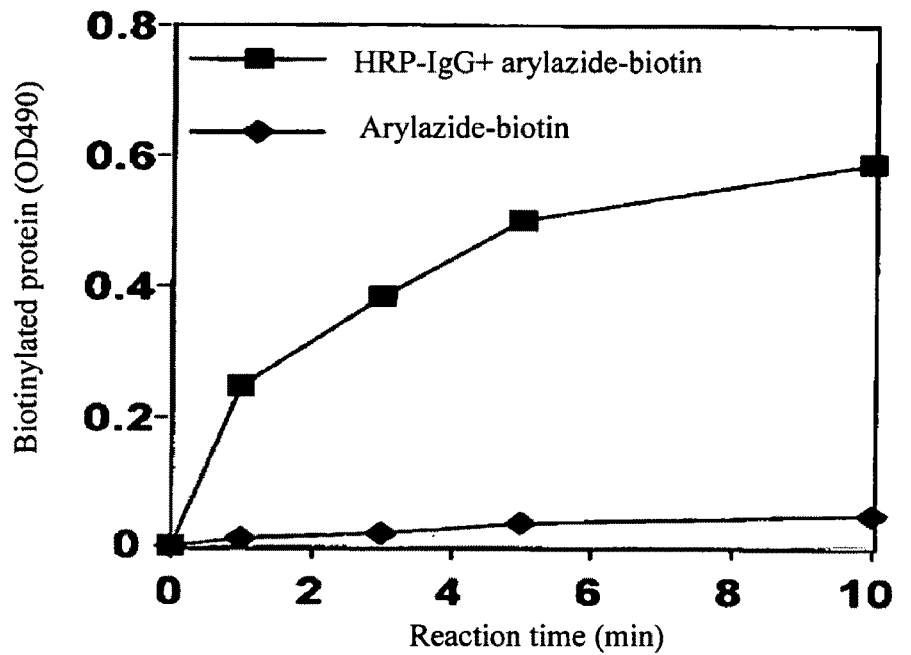
(2)
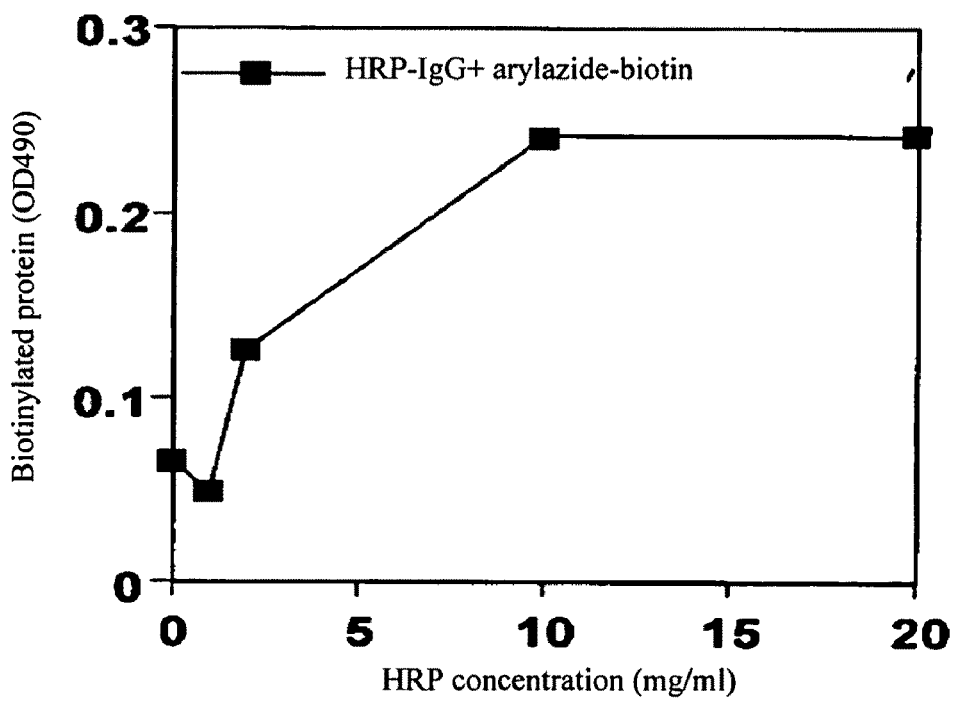

METHOD FOR DETECTION OF COMPOUND INTERACTING WITH MOLECULE LOCATED ON CELL MEMBRANE

TECHNICAL FIELD

The present invention relates to a method for detection of a compound interacting with a molecule located on a cell membrane and a kit for carrying out the method.

BACKGROUND ART

In a phospholipid bilayer constituting a cell membrane, there are a large number of proteins, lipids other than phospholipids, and the like, some of which function as growth factor receptors, cell adhesion factors, ion channels and the like. The molecules located on the cell membrane can move relatively freely in the cell membrane, and assemble and dissociate repeatedly. Particularly, a structure called raft, which is formed by an assembly of a plurality of molecules located on the cell membrane and is exposed on the surface of the cell membrane, plays an important role, for example, as a receptor for bacterium, virus or the like, or as a platform for transmitting extracellular information into the cell. Accordingly, it is very important in biochemical research to know with what kind of other molecules located on the cell membrane, a certain molecule located on the cell membrane functions in coordination.

However, the analysis of interaction between molecules located on the cell membrane is very difficult. For example, an immunoprecipitation method is known as a method for separating and detecting a protein interacting with a certain target protein, in which the target protein is selectively precipitated by acting an antibody specific for the target protein with the target protein. However, in the method, it is difficult to reflect the interacted state of the target protein and the other protein under a physiological condition. This is because, in the method even if the other protein interacts with the target protein located on the cell membrane, such interaction may possibly be cancelled at the stage where the target protein is separated from the cell membrane. Moreover, although no interaction between the proteins occurred on the cell membrane of a living cell, a pseudo-interaction may occur at the stage of separating the proteins.

As another method, a cross-linker method is known, in which a protein interacting with a target protein is identified by coupling a cross-linker with the target protein and hereafter cross-linking the interacting protein. In the method, however, the length and the shape of the cross-linker molecule are fixed; therefore, only the closely contacted protein can be cross-linked and detected. As a result, there are few examples in which the interaction between molecules on the cell membrane could be successfully analyzed by the cross-linker method.

Accordingly, specialized techniques for detection of the interaction between molecules on the cell membrane, other than the methods described above, were examined.

For example, Patent Document 1 describes a screening method of a substance interacting with an ABC (ATP Binding Cassette) protein located on a cell membrane. In the method, a membrane fraction where the ABC protein has been expressed, a labeled nucleoside triphosphate, a nucleoside diphosphate-immobilized substance and the test substance, are contacted together.

Patent Document 2 describes a method of screening a candidate compound interacting with transmembrane proteins, by expressing the transmembrane proteins on a cell and then contacting the candidate compound therewith to detect the change in the distribution of the transmembrane proteins compared with the situation where the candidate compound was not contacted with the transmembrane proteins.

Patent Document 1: JP2005-24245A
Patent Document 2: JP2005-522227T

DISCLOSURE OF THE INVENTION

The detection of the interaction between molecules such as proteins located on a cell membrane is very important not only in biochemical research but also in drug development, and techniques therefor were also developed.

However, the techniques described in Patent Documents 1 and 2 have a disadvantage that compounds possibly interacting with the target protein located on the cell membrane have to be predicted and purified in advance before the test. Therefore, the knowledge concerning many molecules located on the cell membrane should be obtained beforehand, and the interaction between the target molecule located on the cell membrane and an unknown molecule cannot be detected. Furthermore, in the related arts, it is very difficult to detect the interaction among 3 or more molecules.

Accordingly, one object of the present invention is to provide a convenient and low-cost method for detection of a wide variety of compounds interacting with a target molecule located on a cell membrane, using a living cell without need of separating the cell membrane or the like from the cell. Another object of the present invention is to provide a kit for carrying out the method of the present invention.

The inventors of the present invention made investigation to solve the problem described above. As a result, it is found that the object can be achieved by applying a radical reaction. That is, a radical compound has very high reactivity and is thus considered to be capable of covalently binding to many compounds, particularly to proteins. In addition, the radical compound cannot stably exist due to the high reactivity thereof and therefore only binds to an adjacent compound. Accordingly, it is considered that, when the radical reaction is applied, the radical compound is highly likely to only react with the adjacent compound interacting with the target compound, therefore the noise is little.

The method for detection of a compound interacting with a molecule located on a cell membrane according to the present invention comprises steps of allowing a compound having a moiety capable of binding selectively to the target molecule located on the cell membrane and a radicalization-promoting moiety, to act on the cell;

further allowing a compound having a group capable of being radicalized by the radicalization-promoting moiety and a labeling group, to act on the cell; and identifying the interacting compound bound by the compound radicalized by the radicalization-promoting moiety.

The kit of the present invention is the one for carrying out the method of the present invention, comprising the compound having the moiety capable of binding selectively to the molecule located on the cell membrane and the radicalization-promoting moiety;

the compound having the group capable of being radicalized by the radicalization-promoting moiety and the labeling group; and the means for identifying the compound bound by the compound radicalized by the radicalization-promoting moiety.

BRIEF DESCRIPTION OF THE DRAWINGS

FIG. 1 is a graph showing that a mouse serum protein or the like was biotinylated only when an HRP-labeled anti-mouse IgG antibody and an arylazide-biotin were used.

FIG. 2 is a graph showing that a protein or the like was biotinylated only when an HRP-labeled anti-mouse IgG antibody and concanavalin A lectin (Con A) were used.

FIG. 4 is a graph showing time dependence and HRP concentration dependence of the biotin labeling reaction in the method of the present invention.

BEST MODE FOR CARRYING OUT THE INVENTION

Figure 3:
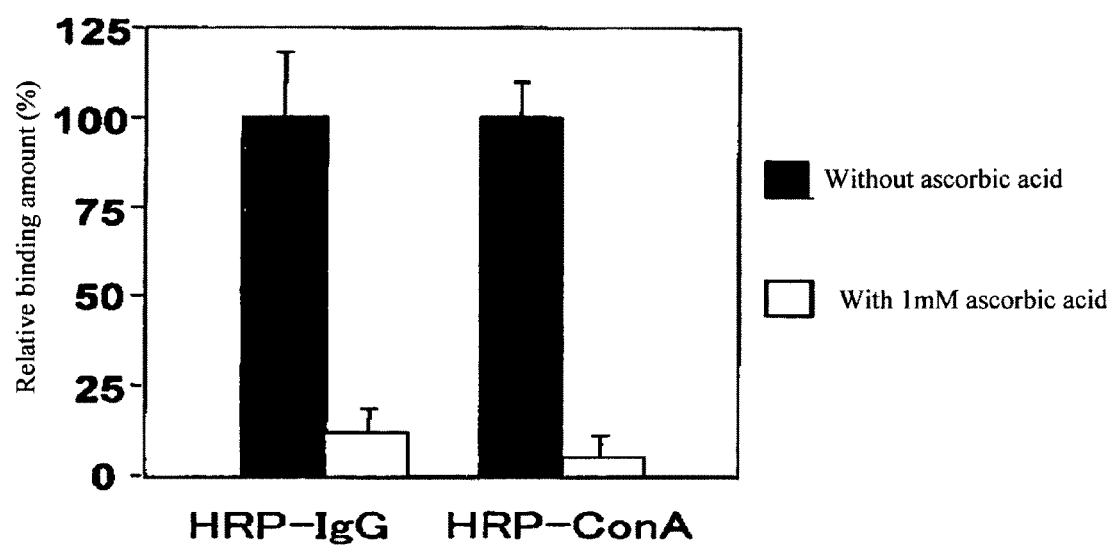
FIG. 3 is a graph showing a labeling degree of biotin when ascorbic acid having a radical elimination action was added.

The method for detection of the compound interacting with the molecule located on the cell membrane according to the present invention comprises the steps of allowing a compound having a moiety capable of binding selectively to the target molecule located on the cell membrane and a radicalization-promoting moiety, to act on the cell (the first step);

further allowing a compound having a group capable of being radicalized by the radicalization-promoting moiety and a labeling group, to act on the cell (the second step); and identifying the interacting compound bound by the compound radicalized by the radicalization-promoting moiety (the third step).

The method of the present invention is used for detection of the compound interacting with the biomolecule existing on a cell membrane. Accordingly, the method of the present invention enables the fundamental study concerning the role of the target molecule located on a cell membrane, the detection of a difference in the interaction among tissues, and the like. For example, it is possible to distinguish the difference between a cancer cell and a normal cell.

Various molecules exist on a cell membrane. The proteins existing on a cell membrane include, for example, superficial proteins existing on the surface layer of a phospholipid bilayer, integral proteins at least a part of which existing in a phospholipid bilayer, and the like. In the present invention, a protein located "on a cell membrane" means that at least a part of the protein is exposed to the outside of a cell membrane. For example, the proteins located on a cell membrane include the protein partially existing in a cell and partially exposed to the outside of a cell membrane, the protein bound directly to a phospholipid, the protein bound to a cell membrane via lipid or oligosaccharide, the protein bound to the protein exposed to the outside of a cell membrane, and the like. The functions of proteins are not particularly limited and can include, for example, the function of transmitting the information coming from an extracellular compound into a cell and transmitting the intracellular information to the outside of a cell, and the like.

The type of molecule on a cell membrane is not particularly limited. For example, lipids and the like exist in addition to the proteins described above. A sugar chain bound to a protein may be exposed partially or wholly to the outside of a cell membrane in some cases, and such sugar chain also falls in the molecules on a cell membrane. Particularly, the lipid containing a sugar chain is one of important components constituting a cell membrane, the lipid moiety thereof exists in a phospholipid bilayer and the sugar chain moiety thereof is exposed to the outside of the cell. A glycolipid exists in a concentrated state in raft and is considered to be involved in the formation of raft.

The type of "interaction" is not particularly limited and not only include the specific bonding such as covalent bonding and electrostatic bonding, but also include the situation where a protein and one or more compounds close relatively near to exert functions.

The compounds interacting with the target molecule located on the cell membrane are not particularly limited and include such as proteins, glycolipids, phospholipids and cholesterols existing on the cell membrane, as well as extracellular information transmitters such as ions and ligands, and the like.

Hereinafter, the method of the present invention is described in detail in the order of operation.

(1) The First Step

In the present invention, firstly, the compound having the moiety capable of binding selectively to the target molecule located on the cell membrane and the radicalization-promoting moiety is allowed to act on the cell. By the step, the moiety having the radicalizing function can be bound selectively to the target molecule located on the cell membrane.

The target molecule located on the cell membrane may be appropriately selected from the ones by which the compound interacting with the molecule can be specified, and the type is not particularly limited. The moiety capable of binding selectively to the molecule located on the cell membrane can be selected appropriately depending on the target molecule located on the cell membrane. For example, an antibody specific for the molecule located on the cell membrane, or a peptide capable of specifically binding to the sugar chain or the like which are bound to the target molecule, can be used. The antibody is preferably used. When a primary antibody is bound to the target molecule located on the cell membrane, the selectively binding moiety may be an antibody capable of secondarily labeling the primary antibody.

The radicalization-promoting moiety refers to the moiety capable of radicalizing the compound used in the second step described below. A peroxide such as hydrogen peroxide, light, or the like is usually used for the radicalization of compound; however, the substances can give damage to the living cell. The method of the present invention is characterized by being capable of detecting the interaction between compounds on the cell membrane of the living cell; and therefore, no means giving damage to the living cell is used in the method. As the radicalization-promoting moiety, a peroxidase such as horseradish peroxidase or a heme compound such as hemin can be used.

The compound used in the step has the moiety capable of binding selectively to the molecule located on the cell membrane and the radicalization-promoting moiety. The moiety can be bound directly, or bound indirectly via a linker group such as a peptide chain or an alkylene group. The compound in which the moiety are bound directly includes, for example, the antibody for the target molecule located on the cell membrane or the like, which is modified by the radicalization-promoting moiety. The compound is commercially available or may be prepared by a conventional method using an HRP (horseradish peroxidase)-labeled kit or the like.

In order to allow the compound having the moiety capable of binding selectively to the molecule located on the cell membrane and the radicalization-promoting moiety, to act on the cell, an aqueous solution of the compound may be added to the cell and then incubate the compound and the cell. The concentration of the compound in the aqueous solution may be adjusted appropriately, but is usually adjusted as about 1 to 100 μg/mL relative to the culture medium. The incubation condition may be adjusted appropriately in consideration of the type of cell used, the optimum temperature of the enzyme and the like, but is usually adjusted as 0 to 37° C. and about 10 minutes to 5 hours.

After the incubation, the cell is washed to remove the excessive compound. For washing, an operation of removing the supernatant and then adding PBS or the like followed by gentle stirring, may be repeated several times.

(2) The Second Step

Then, the compound having the group capable of being radicalized by the radicalization-promoting moiety and the labeling group is allowed to act on the cell treated by the first step. In the step, the compound is radicalized by the radicalization-promoting moiety bound selectively to the target compound, and then bound to the adjacent compound.

The group capable of being radicalized by the radicalization-promoting moiety may be the one suited to the radicalizing enzyme used. For example, at least one group selected appropriately from such as a hydroxyl group, an azide group, a halogen group and an indole group can be used.

The type of labeling group is also not particularly limited and may be the one used in the field of biochemistry. For example, biotin; a fluorescence group based on such as rhodamine, fluorescein, Texas Red and cyanine; a substituent group containing radioisotope such as $^{32}P$, $^{35}S$ or $^{14}C$; a peptide for labeling; and a hapten can be used.

The group capable of being radicalized and the labeling group are bound preferably via a linker group, for the reason that the labeling group is not influenced by the radical, the synthesis is facilitated, and the like. As the linker group, for example, an alkylene group, an ether group, a thioether group, an amide group, or a combination of two or more of these groups can be used.

The specific example of the compound is the following compound. In the following compound, the group capable of being radicalized is an azide-hydroxyphenyl group, and the labeling group is a biotin group. In the following compound, however, the specific structure of the linker group can be replaced by the other one, because the linker group has no particular meaning except to reduce the influence of the radical on the labeling group and facilitate the synthesis of the compound.

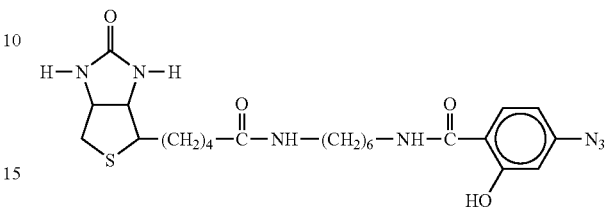

The compound having the group capable of being radicalized and the labeling group may be added in a solution state to the cell. Specifically, an aqueous solution containing the compound at about 10 to 100 μg/mL may be used. When the compound is sparingly soluble in water, an organic solvent such as dimethylsulfoxide or ethanol may be added to such an extent that the cell to be used is not adversely affected.

The compound radicalized by the radicalization-promoting moiety is highly reactive so that the moving distance of the compound with radical is short, and thus the compound only binds to the molecule existing in the vicinity of the target molecule located on the cell membrane. For example, it is found that the maximum moving distance of a hydroxy radical generated by the laser molecule inactivation method is about 1.5 nm in radius, and that the moving distance of a singlet oxygen radical generated by the fluorophore-assisted light inactivation method is about 10 to 50 nm (J. C. Liao et al., Proc. Natl. Acad. Sci. USA, 91, 2659 (1994), S. Beck et al., Proteomics, 2, 247 (2002), and the like). The inventors of the present invention conducted an experiment separately by using gold colloid particles and an electron microscope, and found that the radical generated by horseradish peroxidase was suggested to exist within 100 nm from the probe molecule. From the findings, it can be estimated that the radical generated by the reaction in the present invention can bind to the molecule existing within 100 nm from the target molecule located on the cell membrane, but does not bind to the molecule at the position apart more than 100 nm from the target molecule.

The reaction condition may be appropriately adjusted and can be, for example, 0 to 37° C. and about 5 minutes to 1 hour. To prevent the photo-radicalization, the reaction is conducted preferably in a dark place.

After the reaction, the excessive compound is removed by washing. More specifically, an operation of removing the supernatant followed by gentle stirring with PBS or the like may be repeated several times.

(3) The Third Step

In the step, the interacting compound bound by the compound radicalized by the radicalization-promoting moiety, is identified. More specifically, firstly, the cell is physically pulverized with a homogenizer or the like. As a result, the cell membrane is broken finely to form a vesicle of about 100 nm in diameter. The vesicle is called a microsome. The microsome is separated from the nucleus by centrifugation or the like to obtain a microsome fraction which is then lysed in a lysis buffer or the like.

Then, the labeled compound is identified by using the obtained lysate, with a conventional method such as a western blotting, an antibody array, a mass spectrometry, an immunoprecipitation method or an immunohistochemical staining. The method can be selected mainly in consideration of the type of the labeling group used in the second step, and a combination of two or more methods can be used.

More specifically, for example, the compound contained in the obtained lysate is firstly separated. The specific separation method can be selected appropriately from those used generally in the field of biochemistry. For example, the methods capable of separating the compound according to molecular weight such as SDS polyacrylamide gel electrophoresis and gel filtration chromatography, or a microarray on which antibody is immobilized, may be used.

After the compound is separated, the labeled compound is identified by a method suited to the labeling group used. For example, when the fluorescence group is used as the labeling group, the compound may be analyzed by the fluorescence wavelength inherent in the fluorescence group. When biotin is used as the labeling group, a biotinylated enzyme is allowed to bind specifically to the compound via avidin or streptavidin. When an alkali phosphatase, peroxidase, luciferase or the like is used as the enzyme, the labeled compound can be identified by acting the coloring reagent suited to the enzyme on the enzyme. The labeling group is bound via a covalent bond to the compound interacting with the target molecule located on the cell membrane, by the radical reaction. Therefore, the labeling group is not separated from the compound even after the process described above.

The kit of the present invention is the one for carrying out the method of the present invention, comprising the compound having the moiety capable of binding selectively to the target molecule located on the cell membrane and the radicalization-promoting moiety;

the compound having the group capable of being radicalized by the radicalization-promoting moiety and the labeling group; and the means for identifying the compound bound by the compound radicalized by the radicalization-promoting moiety.

The compounds and the identifying methods in the kit of the present invention can be those described in the method of the present invention.

According to the present invention, a wide variety of compounds interacting with the biomolecule existing on the cell membrane can be detected by using the living cell. In the detection, it is not necessary to predict and separate the possibly interacting compound in advance. In addition, the method of the present invention can be carried out very easily and at low cost. Accordingly, the method of the present invention and the kit for carrying out the method of the present invention are very important, not only in biochemical research but also in industrial applications for drug development and the like.

EXAMPLES

Hereinafter, the present invention is described in more detail with reference to examples, but the present invention is not limited to the examples and can be carried out in such a range as to be adapted to the purport of the description in the specification, and any of such modifications fall under the scope of the present invention.

Example 1

A 20% mouse serum (manufactured by Cedarlane Laboratories) solution in PBS was added to a 96-well microtiter plate (manufactured by Nunc) having a surface treatment with MaxiSorp; and then the plate was incubated at 37° C. for 40 minutes to coat the surface with the mouse serum. After blocking with a 2% BSA-PBS solution, an unlabeled anti-mouse IgG antibody (10 µg/mL; manufactured by CHEMICON), an HRP-labeled anti-mouse IgG antibody (10 µg/mL; manufactured by Promega), an FITC-labeled anti-mouse IgG antibody (10 µg/mL; manufactured by DAKO), or an HRP-labeled anti-rabbit IgG antibody (10 µg/mL; manufactured by Cappel) was added in a volume of 50 µL to the well; and then the plate was incubated at room temperature for 40 minutes. After the plate was washed and then cooled on ice, a 50 µL solution of an arylazide-biotin compound shown below (40 µg/mL; manufactured by Pierce) in PBS was added to each well and the plate was incubated at 4° C. for 10 minutes in a dark place.

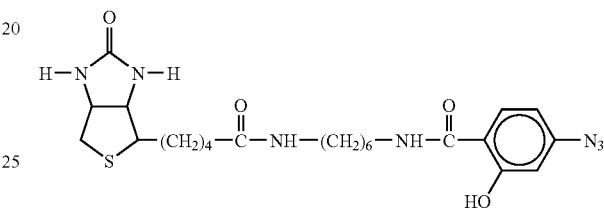

Subsequently, each well was washed and 2M HCl was added to remove the bound antibody, followed by incubation at room temperature for 40 minutes. Each well was washed well again, and the biotinylated molecule in each well was detected with an ABC detection kit (manufactured by Vector Laboratories). The well was colored with o-phenylenediamine and measured for the absorbance at 490 nm. For comparison, wells to which only each antibody was added but the arylazide-biotin was not added, and wells to which only the arylazide-biotin was added but each antibody was not added were also examined in a similar manner. The measurement results of coloring density in each well are shown in FIG. 1.

As shown in FIG. 1, when the HRP-labeled anti-mouse IgG antibody was used, the arylazide-biotin compound was bound by the action of HRP (horseradish peroxidase) to the protein existing on the surface of the plate, thereby selectively enhancing the coloring density.

Example 2

A 20% goat serum (manufactured by Dako) solution in PBS was added to the plate used in Example 1 and the plate was incubated at 37° C. for 40 minutes to coat the surface with the goat serum. After blocking with the 2% BSA-PBS solution, concanavalin A lectin or HRP-labeled concanavalin A lectin (each at 10 µg/mL; manufactured by Seikagaku Corporation) was added in a volume of 50 µL to the well and the plate was incubated at room temperature for 40 minutes. After the plate was washed and cooled on ice, the PBS solution of the arylazide-biotin compound used in Example 1 (40 µg/mL; manufactured by Pierce) was added in a volume of 50 µL to each well and the plate was incubated at 4° C. for 10 minutes in a dark place. Concanavalin A lectin can recognize high-mannose-type sugar chains, mixed-type sugar chains, duplex conjugated-type sugar chains and the like, and thus can bind to many serum glycoproteins on the surface of the plate. After each well was washed, 2M HCl was added to remove the bound concanavalin A lectin, followed by incubation at room temperature for 40 minutes. Thereafter, the amount of biotin bound to the surface of the plate was measured in the same manner as Example 1. The result is shown in FIG. 2.

As shown in FIG. 2, when the HRP-labeled concanavalin A lectin was used, the arylazide-biotin compound was bound by the action of HRP to the protein existing on the surface of the plate, thereby selectively enhancing the coloring density.

Example 3

It was estimated that, in Examples 1 and 2, the reason why biotin was bound to the protein existing on the surface of the plate only when the HRP-labeled IgG or concanavalin A lectin was used, is that the arylazide-biotin compound was radicalized by HRP. The estimation was experimentally confirmed. Specifically, when the HRP-labeled IgG or concanavalin A lectin was used, the relative change in coloring density of adding 1 mM ascorbic acid having an ability to capture radicals together with the arylazide-biotin compound, was measured. The absorbance (OD490) when ascorbic acid was not added was taken as 100%, the relative values when ascorbic acid was added are shown in FIG. 3.

As shown in FIG. 3, the binding of biotin is inhibited by about 90% when ascorbic acid was added. Therefore, it was demonstrated that the arylazide-biotin compound was bound to the surface of the plate by the radicalization of HRP.

Example 4

An experiment similar to Example 1 was conducted, in which the HRP-labeled anti-mouse IgG antibody was used or not used and the reaction time with the arylazide-biotin compound was changed to 1, 3 or 5 minutes. Another similar experiment was conducted in which the concentration of the HRP-labeled anti-mouse IgG antibody was changed to 1, 2 or 20 µg/mL. The results of the experiment in which the reaction time was changed are shown in FIG. 4(1), and the results of the experiment in which the concentration of the HRP-labeled anti-mouse IgG antibody was changed are shown in FIG. 4(2).

As shown in FIGS. 4(1) and (2), the reaction of the HRP-labeled anti-mouse IgG antibody with the arylazide-biotin compound proceeds depending on the reaction time and the amount of HRP. Thus, the reaction was found to be an enzymatic reaction.

Example 5

HeLa S3 cell, a human cervical cancer cell, was cultured in RPMI 1640 medium (manufactured by Sigma) containing 10% FBS, in a 5% $CO_2$ atmosphere at 37° C. Then, after the cultured cell was cooled at 4° C. for 20 minutes and washed once with PBS, a hybridoma culture containing an antibody TS2/16 (8 µg/mL) binding to β1 integrin was added to the cell and the plate was incubated at 4° C. for 1 hour. Subsequently, an HRP-labeled anti-mouse IgG antibody (10 µg/mL; manufactured by Promega) was added and the plate was incubated at 4° C. for 1 hour to secondarily label the antibody TS2/16. After washing with PBS, the 40 µg/mL PBS solution of the arylazide-biotin compound used in Example 1 was added and the plate was incubated at 4° C. for 30 minutes in a dark place. After washing twice with PBS, the cell was recovered in an Eppendorf tube with 50 mM Tris-HCl (pH 7.4) containing 5% FBS (or 2% BSA) and a protease inhibitor cocktail (manufactured by Sigma), and pulverized with a syringe equipped with needle 21 G. The nucleus was removed by centrifugation at 3000 rpm for 5 minutes, and a microsome fraction was collected and lysed in a lysis buffer (20 mM Tris-HCl, pH 7.4, 150 mM NaCl, 5 mM EDTA, 1% NP-40, 10% glycerol and the protease inhibitor cocktail).

Figure 5:
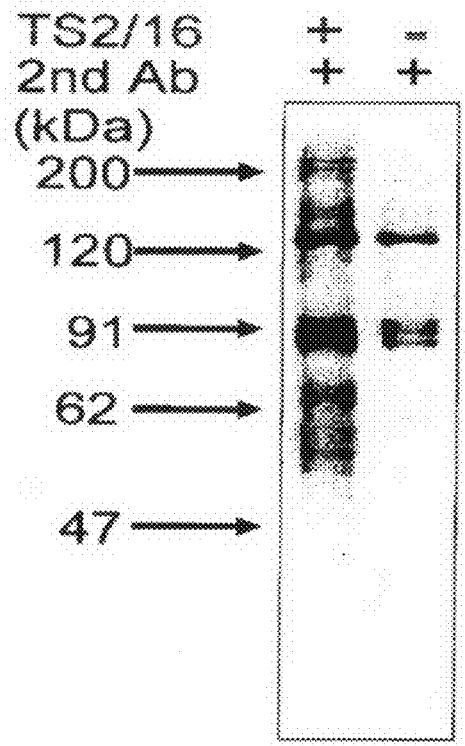
FIG. 5 is an electrophoresis result showing a difference in biotin-labeled compounds interacting with β1 integrin located on a human cervical cancer cell, between a case where both an antibody TS2/16 and a secondary antibody HRP-labeled anti-mouse IgG antibody were used and a case where only the HRP-labeled anti-mouse IgG antibody was used but the antibody TS2/16 was not used.

The sample obtained above was subjected to SDS polyacrylamide gel electrophoresis on 8% gel under nonreducing condition and transferred onto a PVDF membrane, and then the biotinylated protein was detected with the ABC detection kit and ECL western blot detection reagents (manufactured by Amasham Bioscience). For a negative control, a similar experiment was conducted in which the antibody TS2/16 was not used. The result is shown in FIG. 5. In the figure, "2nd Ab" refers to the secondary antibody, i.e. the HRP-labeled anti-mouse IgG antibody.

As shown in FIG. 5, bands in the vicinity of 120 kDa and 91 kDa appear when only the HRP-labeled anti-mouse IgG antibody was used but the antibody TS2/16 was not used. The bands are considered as bands derived from endogenous biotin-carrying molecule or endogenous molecule having reactivity with arylazide-biotin. On the other hand, when the antibody TS2/16 was used, not only the proteins in the vicinity of 120 kDa and 91 kDa but also various proteins were detected. It indicates that, proteins interacting with β1 integrin to which the antibody TS2/16 is directly bound, was detected. Therefore, it was demonstrated that compounds interacting with the target molecule located on the cell membrane can be detected according to the method of the present invention.

Example 6

Human glioma T98 cell was cultured in the same manner as Example 5. After the cultured cell was treated in the same manner as in Example 5, the biotinylated proteins were detected. The result is shown in FIG. 6.

Figure 6:
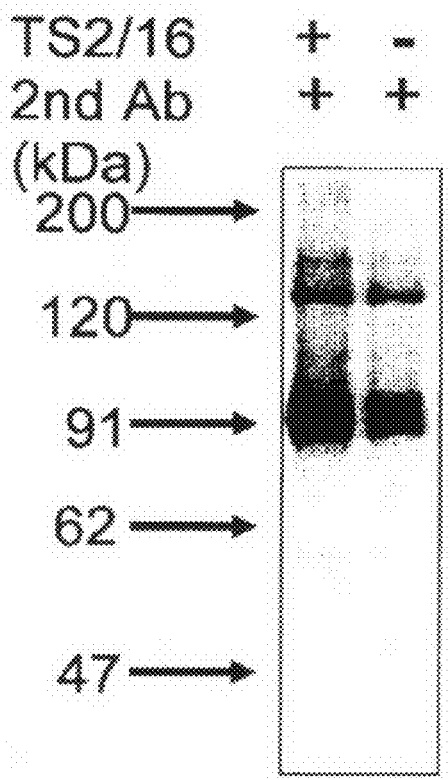
FIG. 6 is an electrophoresis result showing a difference in biotin-labeled compounds interacting with β1 integrin located on a human glioma T98 cell, between a case where both the antibody TS2/16 and the secondary antibody HRP-labeled anti-mouse IgG antibody were used and a case where only the HRP-labeled anti-mouse IgG antibody was used but the antibody TS2/16 was not used.

As shown in FIG. 6, compared to the case where only the HRP-labeled anti-mouse IgG antibody was used but the antibody TS2/16 was not used, a biotin-labeled band in the vicinity of about 200 kDa was recognized when both the antibody TS2/16 and the HRP-labeled anti-mouse IgG antibody were used. From the results of FIGS. 5 and 6, it was revealed that the compounds interacting with β1 integrin are different between the cervical cancer cell and the glioma cell although both of them are human-derived cells.

Example 7

By the same method as Example 5, the HRP-labeled anti-mouse IgG antibody and the arylazide-biotin compound were allowed to act successively on the HeLa S3 cell and a lysate of microsome fraction was then obtained. The sample was added to an antibody array (Human Phospho-RTK Array, manufactured by R&D Systems) on which 42 types of anti-receptor tyrosine kinase antibodies were spotted; and then the plate was incubated overnight at 4° C. After washing, the biotinylated receptor tyrosine kinases were detected by the same method as Example 5. For comparison, an experiment was conducted under the same conditions as above except the antibody TS2/16 was not used. Further, an experiment confirming the expression level of each receptor tyrosine kinase was conducted, by using a nonspecific biotin-labeled reagent N-hydroxysuccinimide (NHS)-biotin in place of the combination of the HRP-labeled anti-mouse IgG antibody and the arylazide-biotin compound. The result of using the antibody TS2/16 is shown in FIG. 7(1), the result without using the antibody is shown in FIG. 7(2), and the result of using NHS-biotin is shown in FIG. 7(3).

Figure 7:
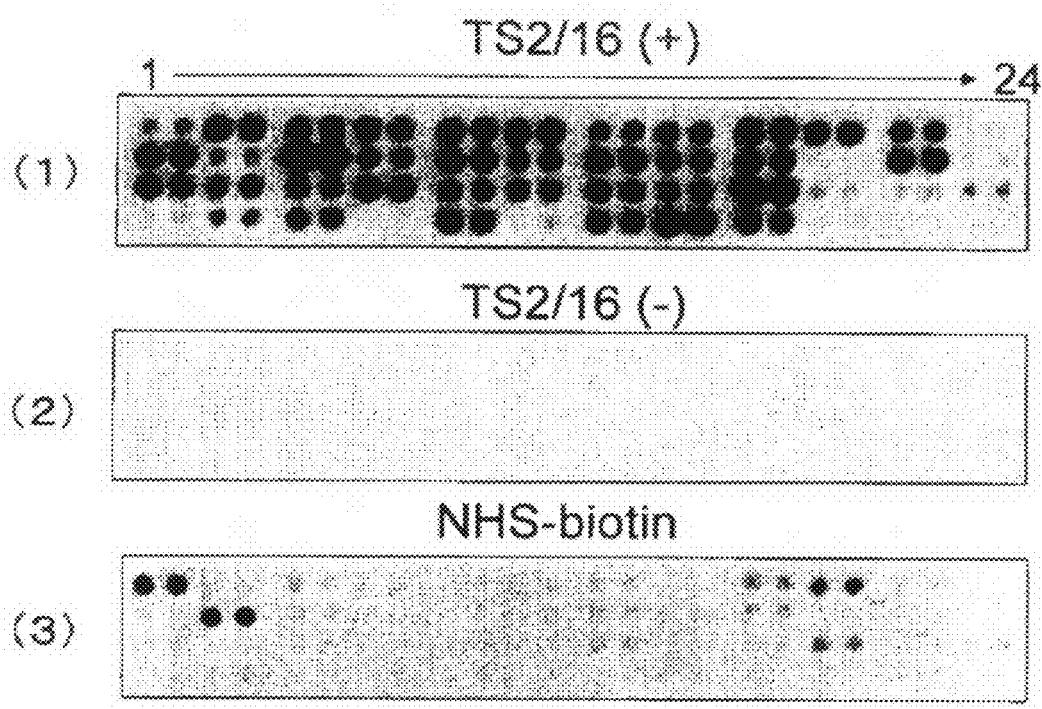
FIG. 7 shows photographs showing the results of analysis of receptor tyrosine kinases interacting with β1 integrin by using an antibody microarray, in which (1) is a case where an HRP-labeled anti-mouse IgG antibody and an arylazide-biotin compound were used, (2) is a case where only the arylazide-biotin compound was used; and (3) is a photograph showing the result of analyzing the expression level of each receptor tyrosine kinases by using NHS-biotin.

As shown in FIG. 7, from the result of using the HRP-labeled anti-mouse IgG antibody and the arylazide-biotin compound to analyze the compound interacting with β1 integrin, it was found that many kinds of receptor tyrosine kinases interacted therewith. From the result that no biotin-labeled receptor tyrosine kinase was detected when the HRP-labeled anti-mouse IgG antibody was not used, it was found that the noise in the method of the present invention is extremely little. By comparing FIGS. 7(1) and (3), it was found that the intensity of interaction between β1 integrin and the receptor tyrosine kinase was not correlated with the expression level of each receptor tyrosine kinase comprehended from FIG. 7(3).

As described above, it was demonstrated that the compound interacting with the target molecule located on the cell membrane can be detected accurately and highly sensitively by the method of the present invention.

Example 8

An HRP-labeled cholera toxin B subunit (CTxB) or unlabeled CTxB binding specifically to glycolipid GM1, and the arylazide-biotin compound were allowed to act successively on the HeLa S3 cell cultured in the same method as in Example 5, to obtain a lysate of microsome fraction. The resulting lysate was examined by using the same antibody array as in Example 7 to detect the receptor tyrosine kinase interacting with GM1. Further, an experiment of confirming the expression level of each receptor tyrosine kinase by using NHS-biotin was conducted in the same manner as in Example 7. The result of using the HRP-labeled CTxB and the arylazide-biotin compound is shown in FIG. 8(1), the result of using the unlabeled CTxB and the arylazide-biotin compound is shown in FIG. 8(2), and the result of using NHS-biotin is shown in FIG. 8(3).

Figure 8:
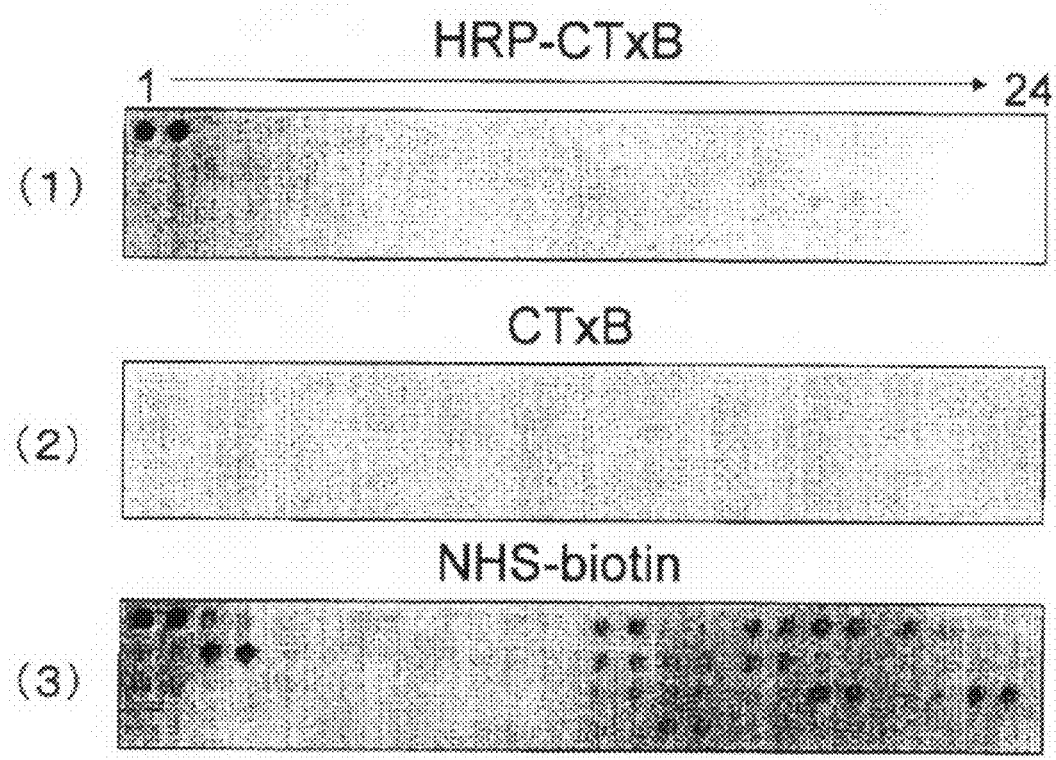
FIG. 8 shows photographs showing the results of analysis of receptor tyrosine kinases interacting with GM1 by using an antibody microarray, in which (1) is a case where an HRP-labeled CTxB and an arylazide-biotin compound were used, (2) is a case where an unlabeled CTxB and the arylazide-biotin compound were used; and (3) is a photograph showing the result of analyzing the expression level of each receptor tyrosine kinase by using NHS-biotin.

As shown in FIG. 8, when the HRP-labeled CTxB and the arylazide-biotin compound were used, mainly two receptor tyrosine kinases were only detected as the compound interacting with glycoprotein GM1. The two receptor tyrosine kinases are epidermal growth factor receptor and ephrin A2. From the result, it was found that only the very limited receptor tyrosine kinases interacted with GM1. Compared to the result, in the experiment of confirming the expression level of each receptor tyrosine kinase by using NHS-biotin, it was found that the receptor tyrosine kinase other than the above two receptor tyrosine kinases was also expressed in the cell. Therefore, it was found that the interaction between GM1 and the receptor tyrosine kinase does not depend on the expression level of the receptor tyrosine kinase.

As described above, it was demonstrated that the compound interacting with the target molecule located on the cell membrane can be selectively detected according to the method of the present invention.

The invention claimed is:

1. A method for detection of a target compound interacting with a target molecule located on a cell membrane, comprising steps of:
    combining a first compound with a cell to contact the first compound with the cell, wherein the first compound has a first moiety and a second moiety, wherein the first moiety is capable of binding selectively to the target molecule located on the cell membrane and the second moiety is a radicalization-promoting moiety, and wherein the first moiety of the first compound selectively binds the first compound to the target molecule located on the cell membrane;
    washing the cell to remove excess first compound;
    combining a second compound with the cell to contact the second compound with the cell, wherein the second compound has a first group and a second group, wherein the first group is capable of being radicalized by the radicalization-promoting moiety of the first compound and the second group is a labeling group, wherein the first group of the second compound is radicalized by the radicalization-promoting moiety of the first compound, wherein the thus-radicalized first group of the second compound binds to a target compound interacting with the target molecule and existing within 100 nm from the target molecule, and wherein the first group is bound to the second group via a linker;
    washing the cell to remove excess second compound; and
    identifying the target compound, using a means for detecting the labeling group of the second compound.

2. The method according to claim 1, wherein horseradish peroxidase or a heme compound is used as the radicalization-promoting moiety.

3. The method according to claim 1, wherein at least one group selected from a hydroxyl group, an azide group, a halogen group and an indole group is used as the group capable of being radicalized by the radicalization-promoting moiety.

4. The method according to claim 1, wherein biotin, a fluorescence group, a radioisotope-containing group, a labeling peptide or a hapten is used as the labeling group.

5. The method according to claim 1, wherein the labeling group is detected by western blot, antibody array, mass spectrometry, immunoprecipitation or immunohistochemical staining.

6. A kit for carrying out the method according to claim 1, comprising:
    a first compound, wherein the first compound has a first moiety and a second moiety, wherein the first moiety is capable of binding selectively to a target molecule located on the cell membrane and the second moiety is a radicalization-promoting moiety;
    a second compound, wherein the second compound has a first group and a second group, wherein the first group is capable of being radicalized by the radicalization-promoting moiety of the first compound and the second group is a labeling group, and wherein the first group is bound to the second group via a linker; and
    a means for detecting the labeling group.

* * * * *